United States Patent [19]
Liu

[11] Patent Number: 6,033,385
[45] Date of Patent: Mar. 7, 2000

[54] SAFETY VEIN SYRINGE WITH RETRACTABLE SPECIAL NEEDLE

[76] Inventor: Wen-Neng Liu, 19508 Nicholas Ave., Cerritos, Calif. 90701

[21] Appl. No.: 09/089,261

[22] Filed: Jun. 3, 1998

[30] Foreign Application Priority Data

Mar. 12, 1998 [TW] Taiwan .................................. 87203549

[51] Int. Cl.[7] .................................................. A61M 5/32
[52] U.S. Cl. .......................................... 604/195; 604/110
[58] Field of Search .................................... 604/110, 181, 604/187, 195, 218

[56] References Cited

U.S. PATENT DOCUMENTS

| | | | |
|---|---|---|---|
| 4,200,478 | 4/1980 | Jacino et al. | 156/94 |
| 4,804,370 | 2/1989 | Haber et al. | 604/195 |
| 4,961,883 | 10/1990 | Jacino et al. | 264/36 |
| 5,104,378 | 4/1992 | Haber et al. | 604/11 |
| 5,215,533 | 6/1993 | Robb | 604/195 |
| 5,242,402 | 9/1993 | Chen . | |
| 5,263,942 | 11/1993 | Smedley et al. | 604/195 |
| 5,269,760 | 12/1993 | Bina | 604/110 |
| 5,308,329 | 5/1994 | Mazur et al. | 604/110 |
| 5,417,661 | 5/1995 | Stringer et al. | 604/110 |
| 5,478,314 | 12/1995 | Malenchek | 604/110 |
| 5,514,100 | 5/1996 | Mahurkar | 604/195 |
| 5,531,694 | 7/1996 | Clemens et al. | 604/110 |
| 5,562,627 | 10/1996 | Chen | 604/110 |
| 5,569,203 | 10/1996 | Chen | 604/110 |
| 5,575,774 | 11/1996 | Chen | 604/110 |
| 5,624,406 | 4/1997 | Labouze | 604/110 |
| 5,722,951 | 3/1998 | Marano | 604/110 |

*Primary Examiner*—Wynn Wood Coggins
*Assistant Examiner*—Deborah Blyveis
*Attorney, Agent, or Firm*—Rosenberg, Klein & Lee

[57] ABSTRACT

A safety vein syringe with retractable special needle, including a syringe barrel, a plunger, an injection needle and a guiding mechanism formed between the needle holder and the plunger. By means of the guiding mechanism, the plunger can be only axially moved within the barrel without rotation and two needle pulling members can be easily aligned with each other and latched together. The first needle pulling member is formed on the needle holder or the plunger, having at least one rotatable click. The second needle pulling member is formed on the plunger or the needle holder, having a detent. When the piston of the plunger is pushed to the bottom, the detent is easily and firmly engaged and hooked with the click. Thereafter, the injection needle and the needle holder can be together pulled into the barrel with the tip of the injection needle positioned under the shoulder section of the barrel. Then the plunger is further pushed to press the tip against the shoulder section and bend the tip so as to destroy the injection needle.

6 Claims, 10 Drawing Sheets

SAFETY VEIN SYRINGE WITH RETRACTABLE SPECIAL NEEDLE

BACKGROUND OF THE INVENTION

1. Field of the Invention

The present invention relates to a safety vein syringe (intravenous syringe) in which the needle is retractable after injection.

2. Description of the Prior Art

Various types of disposable syringes are widely used nowadays. After being discarded, large amount of such syringes result in the problem of pollution of environment. The used syringes often impale medical personnel and infect the personnel with viruses or bacteria carried by the patients. Especially, in the case where the medical personnel are infected with AIDS virus, the personnel may die innocently. In order to solve these problems, various types of retractable syringes have been developed. For example, a spring is installed between the syringe barrel and the piston for pulling the needle back into the barrel after injection. However, due to the property of the liquid medicine, the material of the spring is strictly limited. Therefore, the structure of such syringe is complicated and the manufacturing cost is very high. Various types of safety vein syringes without springs have been also developed. In such syringes, a latch member is disposed at the bottom of the barrel, whereby when the plunger is pushed to the bottom of the barrel, the latch member latches the plunger with the needle. Therefore, when the plunger is pulled back, the needle is retracted into the barrel along with the plunger so as to avoid impalement of the medical personnel or other persons.

In order to avoid leakage of the liquid medicine and unexpected dropping of the needle from the barrel, the needle must be firmly assembled with the barrel. However, in the case that the needle is excessively firmly assembled with the barrel, it will be difficult to pull the needle back into the barrel. Therefore, it is troublesome to consider both situations.

With respect to the general syringe, many kinds of safety vein syringes have been developed in which the injection needle can be retracted into the syringe barrel after injection. However, with respect to the intravenous syringe, the central line of the injection needle is disaligned from the central line of the syringe barrel. Therefore, after injection and when it is desired to engage a needle pulling member disposed at the front end of the plunger with another needle pulling member disposed on the needle holder, it often takes place that the needle pulling member of the plunger cannot be aligned and engaged with the needle pulling member of the needle holder.

U.S. Pat. No. 5,242,402, Chen, shows a safety syringe with retractable self-biased needle adapted for intravenous injection. It provide a needle pulling members of the plunger and the needle holder respectively as an annular flange and an annular groove, in order to connect together in a manner that the annular flange inserts in the annular groove after injection. However, it is difficult to engage the annular flange and the annular groove with each other and the engaging strength therebetween is insufficient. Therefore, it often takes place that the needle holder is loosened from the plunger and cannot be pulled into the syringe barrel.

Therefore, as of the present time, all the conventional safety vein syringes have the above shortcomings and can be hardly used practically.

SUMMARY OF THE INVENTION

In order to solve the above problems, it is an object of the present invention to provide a safety vein syringe with a retractable special needle. The safety vein syringe enables a user to easily align and engage the plunger with the injection needle, whereby the plunger can be firmly engaged with the injection needle for pulling the injection needle into the barrel to avoid impalement of medical personnel.

According to the above objects, the safety vein syringe of the present invention includes: a syringe barrel having a first end, a second end and a first axis extending from the first end to the second end, the syringe barrel being formed with an internal barrel chamber surrounding the first axis by equal distance, the first end of the barrel being disposed with a needle socket extending away from the first and second ends, the needle socket defining a needle holder cavity surrounding a second axis by equal distance, the second axis being disaligned from the first axis by a first eccentrical distance, an eccentrical annular shoulder section being formed between the barrel chamber and the needle holder cavity, the second end of the syringe barrel being formed with an opening; a plunger having a 15 first and a second ends, the first end being disposed with a piston and fitted into the barrel, the plunger having a third axis, after the plunger is installed into the barrel, the third axis coinciding with the first axis of the barrel, the first end of the plunger having a fourth axis disaligned from the third axis by a second eccentrical distance which is equal to the first eccentrical distance; and a needle holder having a first and a second ends, the injection needle being fitted into the first end of the needle holder, the second end of the needle holder being formed with a fitting section fitted in the needle holder cavity of the needle socket, the needle holder having a fifth axis coinciding with the second axis after the fitting section of the second end of the needle holder is fitted into the needle holder cavity.

The safety vein syringe of the present invention further includes a guiding mechanism including: a first guiding section disposed inside the second end of the barrel; and a second guiding section disposed on outer wall of the plunger and slidably fitted with the first guiding section, whereby by means of the guiding of the first and second guiding sections, the plunger and the barrel can be only axially slided relative to each other without rotation with the fourth axis coinciding with the second axis.

The first guiding section is formed by at least two projecting sections projecting from inner wall of the barrel to define a guiding channel.

The second guiding section is formed by an axially extending rib of the plunger, the rib being slidably fitted in the guiding channel of the first guiding section.

The projecting section of the first guiding section further has a guiding slope face and a stopper face, the guiding slope face being directed to the opening of the second end of the barrel, the stopper face being directed to the first end of the barrel, whereby the piston can be slided into the barrel from the opening thereof along the guiding slope face, the stopper face serving to stop the piston from slipping out of the barrel.

The first guiding section has four projecting sections defining four guiding channels which are arranged on inner wall of the barrel at 90 degree intervals.

The cross-section of the plunger with the axially extending ribs of the second guiding section is cross-shaped and the axially extending ribs are respectively slidably fitted in the guiding channels of the first guiding section.

The safety vein syringe of the present invention further includes a needle pulling mechanism including: a first needle pulling member having a first end and a second end, the first end being integrally connected with one of a portion of the first end of the plunger at the fourth axis and a portion of the second end of the needle holder at the fifth axis; and a second needle pulling member having a first end and a second ends, the first end being connected with the other of the portion of the first end of the plunger at the fourth axis and the portion of the second end of the needle holder at the fifth axis, by means of the guiding of the first and second guiding sections, when the first end of the plunger is pushed to the first end of the barrel, the first and second needle pulling members being moved toward each other along the same straight line in alignment with each other and hooked with each other, whereby when the plunger is pulled from the first end of the barrel to the second end thereof, the needle holder and the injection needle are together pulled into the barrel.

The first needle pulling member has at least one click having a first end and a second end, the first end being rotatably connected with the second end of the first needle pulling member, a distance between the first end of the click and either of the fourth axis and fifth axis being defined as a first distance, the second end of the click extending to the first end of the first needle pulling member, a distance between the second end of the click in a free state and either of the fourth axis and fifth axis being defined as a second distance which is less than the first distance, a distance between the second end of the click and the first end of the first needle pulling member being defined as a third distance, a distance between the first end of the click and the first end of the first needle pulling member being defined as a fourth distance which is larger than the third distance, whereby the click is formed as a ratchet.

The first end of the second needle pulling member is formed as a stem and the second end of the second needle pulling member is formed as a detent having a hook section, the hook section being formed with a radially extending hook face, when the first end of the plunger is pushed to the first end of the barrel, the hook section of the detent stretching open and sliding over the second end of the click, when the plunger is pulled from the first end of the barrel to the second end thereof, the hook face of the hook section of the detent abutting against the second end of the click with the stem tightly clamped by the second end of the click, whereby the first needle holder, the second needle holder and the injection needle can be together pulled into the barrel. The first needle pulling member includes at least two radially arranged clicks. The safety vein syringe of the present invention further includes a leakproof structure including at least one first sealing ring and at least one second sealing ring, the first sealing ring being integrally formed on one of the wall of the needle holder cavity and the outer wall of the fitting section of the needle holder, the first sealing ring sealedly contacting with the other of the wall of the needle holder cavity and the outer wall of the fitting section of the needle holder, the second sealing ring being integrally formed on the other of the wall of the needle holder cavity and the outer wall of the fitting section of the needle holder, the second sealing ring sealedly contacting with said one of the wall of the needle holder cavity and the outer wall of the fitting section of the needle holder.

One of the first and second sealing rings is adjacent to the other of the first and second sealing rings.

The safety vein syringe of the present invention further includes an ensurance latch plate, a first latch section and a second latch section, the latch plate having a first end and a second end, the first end being connected with the second end of the barrel, the first latch section being disposed at the second end of the latch plate, while the second latch section being disposed at the second end of the plunger, the second latch section being latched with the first latch section to locate the detent near the click without latching with each other by mis-operation.

The present invention can be best understood through the following description and accompanying drawings, wherein:

DETAILED DESCRIPTION OF THE PREFERRED EMBODIMENTS

Please refer to FIGS. 1 to 10. The safety vein syringe 20 of the present invention includes a syringe barrel 21, a plunger 22, a needle holder 23, an injection needle 24, a guiding mechanism 25 and a needle pulling mechanism 26. The syringe barrel 21 has a first and a second ends 27, 28 and a first axis 29 extending from the first end 27 to the second end 28. The syringe barrel 21 is formed with an internal chamber 30 surrounding the first axis 29 by equal distance. The first end 27 of the syringe barrel 21 is disposed with a needle socket 31 extending away from the first and second ends 27, 28. The needle socket 31 defines a needle holder cavity 32. The needle holder cavity 32 surrounds a second axis 33 by equal distance. The second axis 33 is disaligned from the first axis 29 by a first eccentrical distance 34. An eccentrical annular shoulder section 35 is formed between the internal chamber 30 and the needle holder cavity 32. The second end 28 of the syringe barrel 21 is formed with an opening 36.

Figure 1:
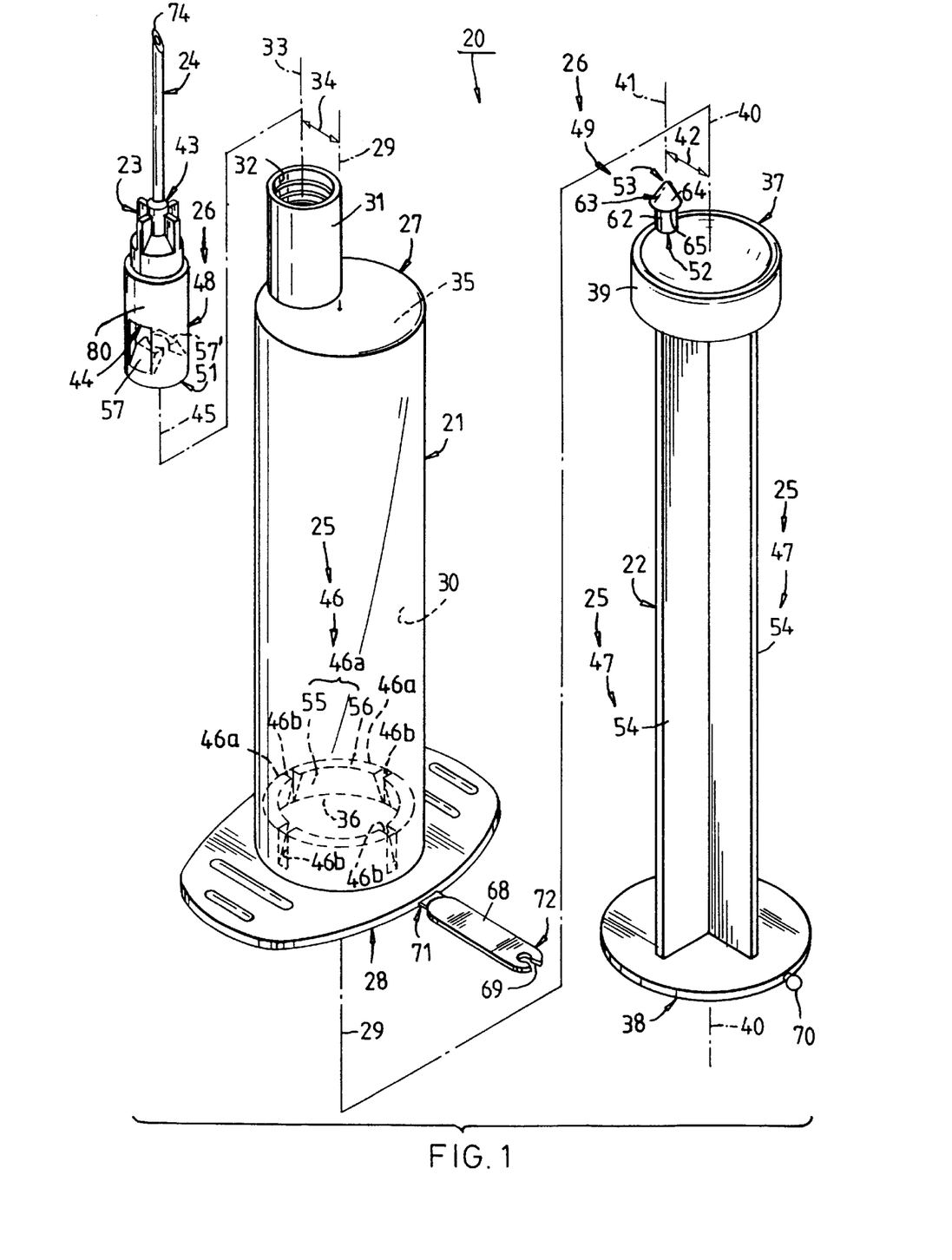
FIG. 1 is a perspective exploded view of a first embodiment of the present invention.
Figure 2:
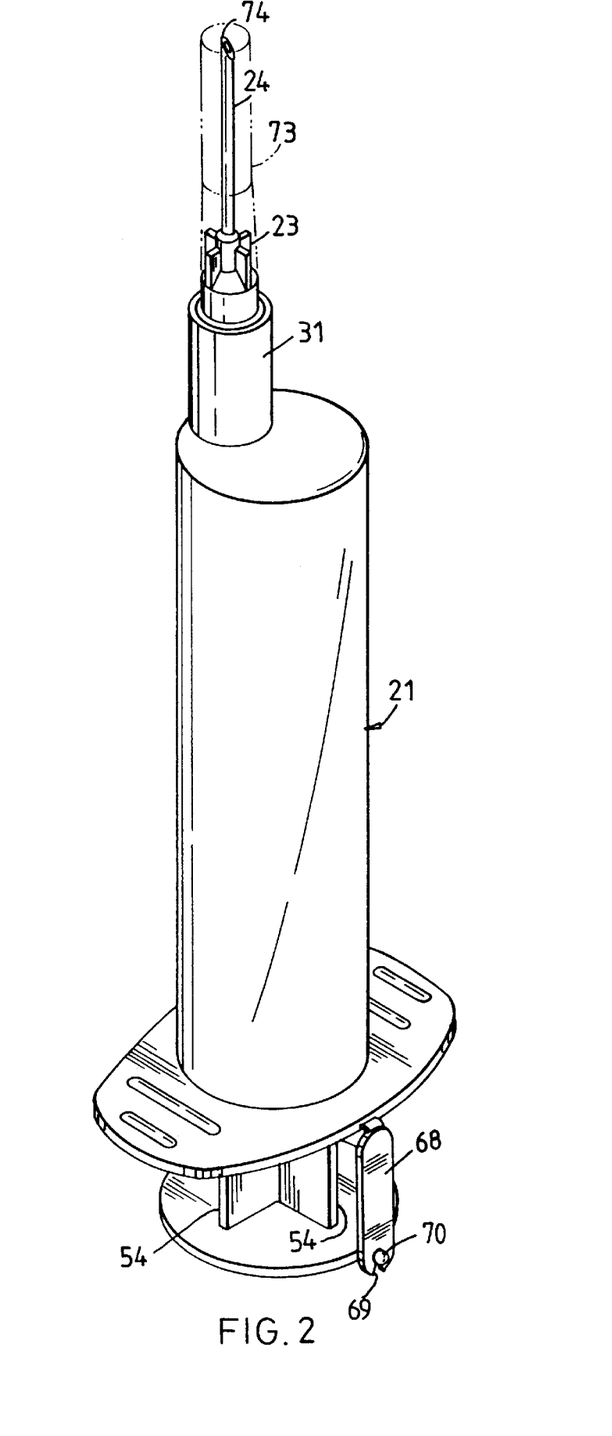
FIG. 2 is a perspective assembled view of the first embodiment of FIG. 1.
Figure 3:
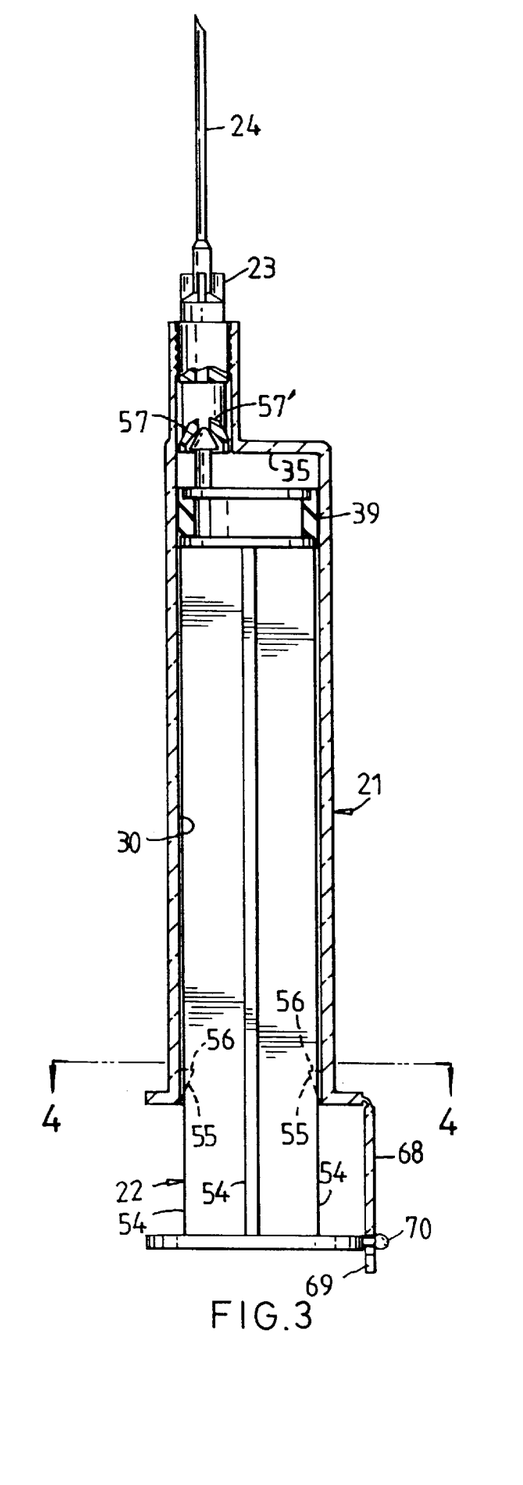
FIG. 3 is a longitudinally sectional view of the first embodiment of FIG. 1.

The plunger 22 has a first and a second ends 37, 38. The first end 37 is disposed with a piston 39 and fitted into the barrel 21. The plunger 22 has a third axis 40. After the plunger 22 is installed into the barrel 21, the third axis 40 coincides with the first axis 29 of the barrel 21. The first end 37 of the plunger 22 has a fourth axis 41 disaligned from the third axis 40 by a second eccentrical distance 42 which is equal to the first eccentrical distance 34.

The needle holder 23 has a first and a second ends 43, 44. The injection needle 24 is inserted with the first end 43 of the needle holder 23. The second end 44 of the needle holder 23 is formed with a fitting section 80 fitted in the needle holder cavity 32 of the needle socket 31. The needle holder 23 has a fifth axis 45 coinciding with the second axis 33 after the fitting section 80 of the second end 44 of the needle holder 23 is fitted in the needle holder cavity 32.

Figure 4:
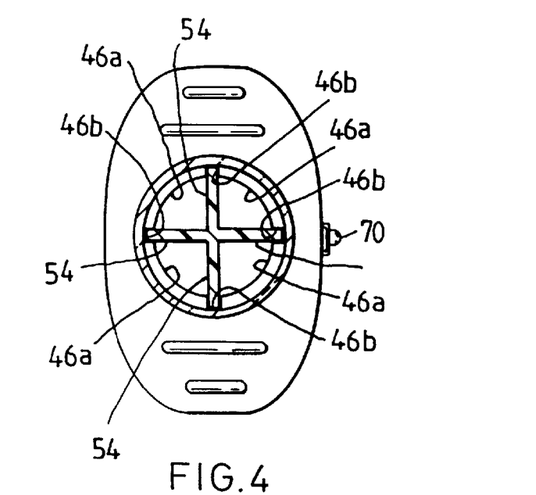
FIG. 4 is a sectional view taken along line 4—4 of FIG. 3.

The guiding mechanism 25 includes a first and a second guiding sections 46, 47. The first guiding section 46 is disposed inside the second end 28 of the barrel 21. The second guiding section 47 is disposed on cuter wall of the plunger 22 and slidably fitted with the first guiding section 46, whereby by means of the first and second guiding sections 46, 47, the plunger 22 and the barrel 21 can be only axially slided relative to each other without rotation with the fourth axis 41 coinciding with the second axis 33.

The needle pulling mechanism 26 includes first and second needle pulling members 48, 49. The first needle pulling member 48 has first and second ends 50, 51. The first end 50 is connected with a portion of the second end 44 of the needle holder 23 at the fifth axis 45.

The second needle pulling member 49 has a first and a second ends 52, 53. The first end 52 is connected to a portion of the first end 37 of the plunger 22 at the fourth axis 41. By means of the guiding of the first and second guiding sections 46, 47, when the first end 37 of the plunger 22 is pushed to the first end 27 of the barrel 21, the first and second needle pulling members 48, 49 are moved toward each other along the same straight line in alignment with each other and hooked with each other. Accordingly, when the plunger 22 is pulled from the first end 27 of the barrel 21 to the second end 28 thereof, the needle holder 23 and the injection needle 24 are together pulled into the barrel 21.

The first guiding section 46 can be formed by at least two projecting sections 46a projecting from inner wall of the barrel 21 to define a guiding channel 46b. The second guiding section 47 can be formed by an axially extending rib 54 of the plunger 22. The rib 54 is slidably fitted in the guiding channel 46b. The projecting section 46b of the first guiding section 46 can further have a guiding slope face 55 and a stopper face 56. The guiding slope face 55 is directed to the opening 36 of the second end 28 of the barrel 21. The stopper face 56 is directed to the first end 27 of the barrel 21, whereby the piston 39 can be slided into the barrel 21 from the opening 36 thereof along the guiding slope face 55. The stopper face 56 serves to stop the piston 39 from slipping out of the barrel 21. In this embodiment, the projecting sections 46a of the first guiding section 46 define four guiding channels 46b which are arranged or inner wall of the barrel 21 at 90 degree intervals. The cross-section of the plunger 22 with the axially extending ribs 54 of the second guiding section 47 can be cross-shaped and the axially extending ribs 54 are respectively slidably fitted in the guiding channels 46b.

Figure 7:
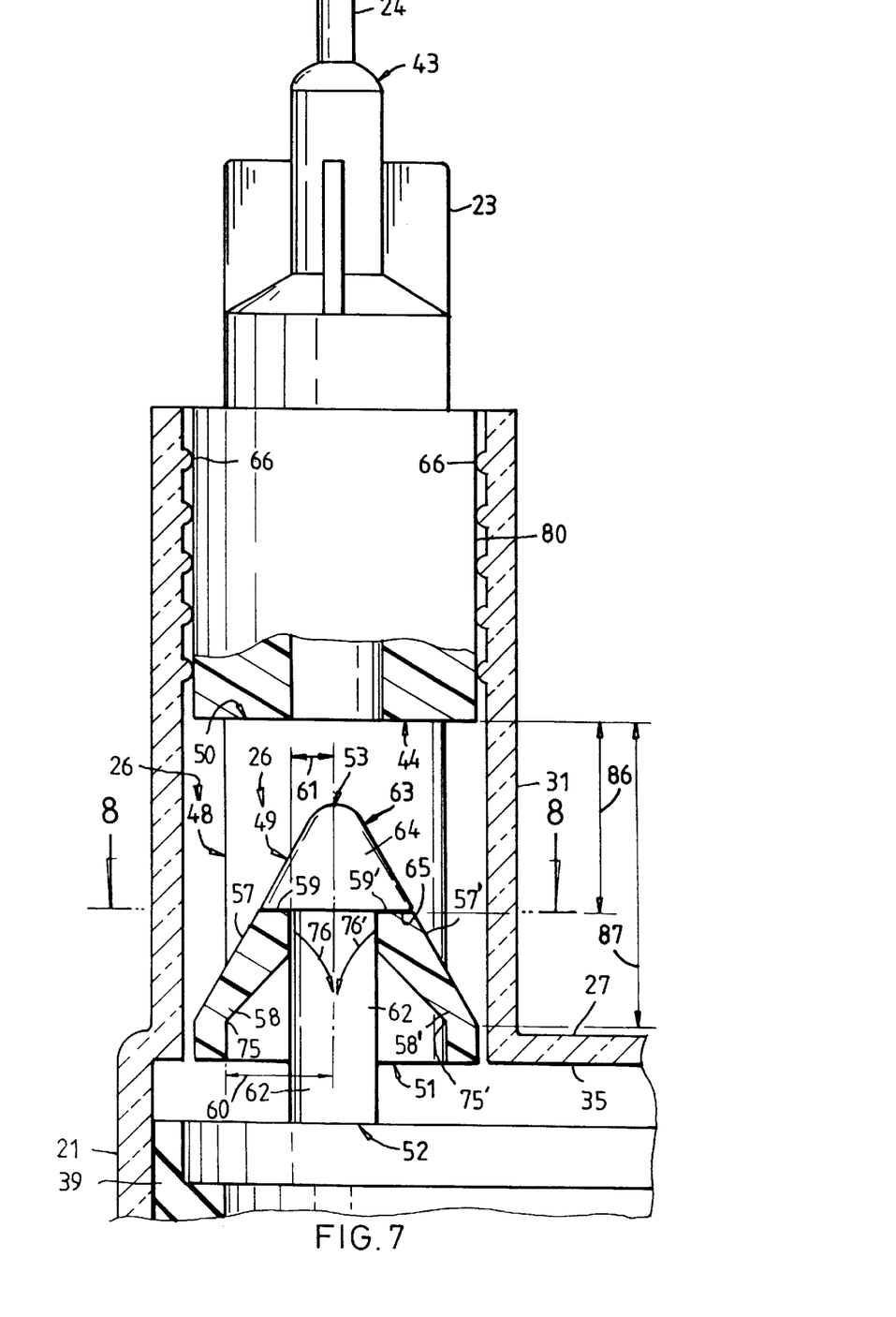
FIG. 7 is an enlarged view of area 7 defined by phantom line of FIG. 6, showing that the plunger is pulled downward and the detent is clamped by two clicks.
Figure 8:
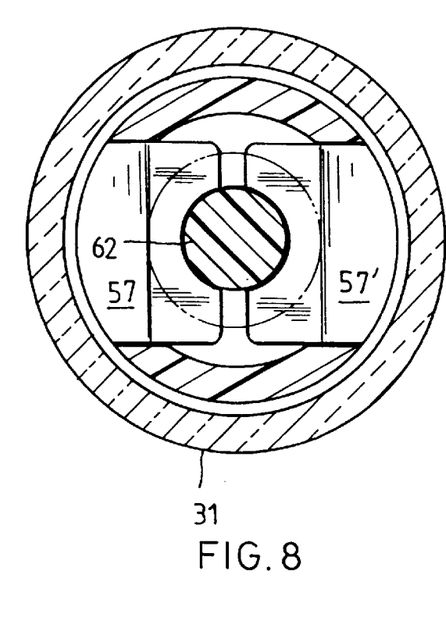
FIG. 8 is a sectional view taken along line 8—8 of FIG. 7.

The first needle pulling member 48 has two clicks 57, 57' each having a first end 58, 58' and a second end 59, 59'. The first end 58, 58' is rotatably connected with the second end 51 of the first needle pulling member 48. The distance between the first end 58, 58' of the click 57, 57' and either of the fourth axis 41 and fifth axis 45 is defined as a first distance 60. The second end 59, 59' of the click 57, 57' extends to the first end 50 of the first needle pulling member 48. The distance between the second end 59, 59' of the click 57, 57' in a free state and either of the fourth axis 41 and fifth axis 45 is defined as a second distance 61 which is less than the first distance 60. The distance between the second end 59, 59' of the click 57, 57' and the first end 50 of the first needle pulling member 48 is defined as a third distance 86. The distance between the first end 59, 59' of the click 57, 57' and the first end 50 of the first needle pulling member 48 is defined as a fourth distance 87 which is larger than the third distance 86, whereby the click 57, 57' is formed as a ratchet.

The first end 52 of the second needle pulling member 49 is formed as a stem 62 and the second end 53 of the second needle pulling member 49 is formed as a detent 63 having a hook section 64. The hook section 64 is formed with a radially extending hook face 65. When the first end 37 of the plunger 22 is pushed to the first end 27 of the barrel 21, the hook section 64 of the detent 63 stretches open and slides over the second end 59, 59' of the click 57, 57'. When the plunger 22 is pulled from the first end 27 of the barrel 21 to the second end 28 thereof, the hook face 65 of the hook section 64 of the detent 63 abuts against the second end 59, 59' of the click 57, 57' with the stem 62 tightly clamped by the second end 59, 59' of the click 57, 57'. Therefore, the needle holder 23 and the injection needle 24 can be together pulled into the barrel 21 so as to avoid impalement of the medical personnel.

Figure 11:
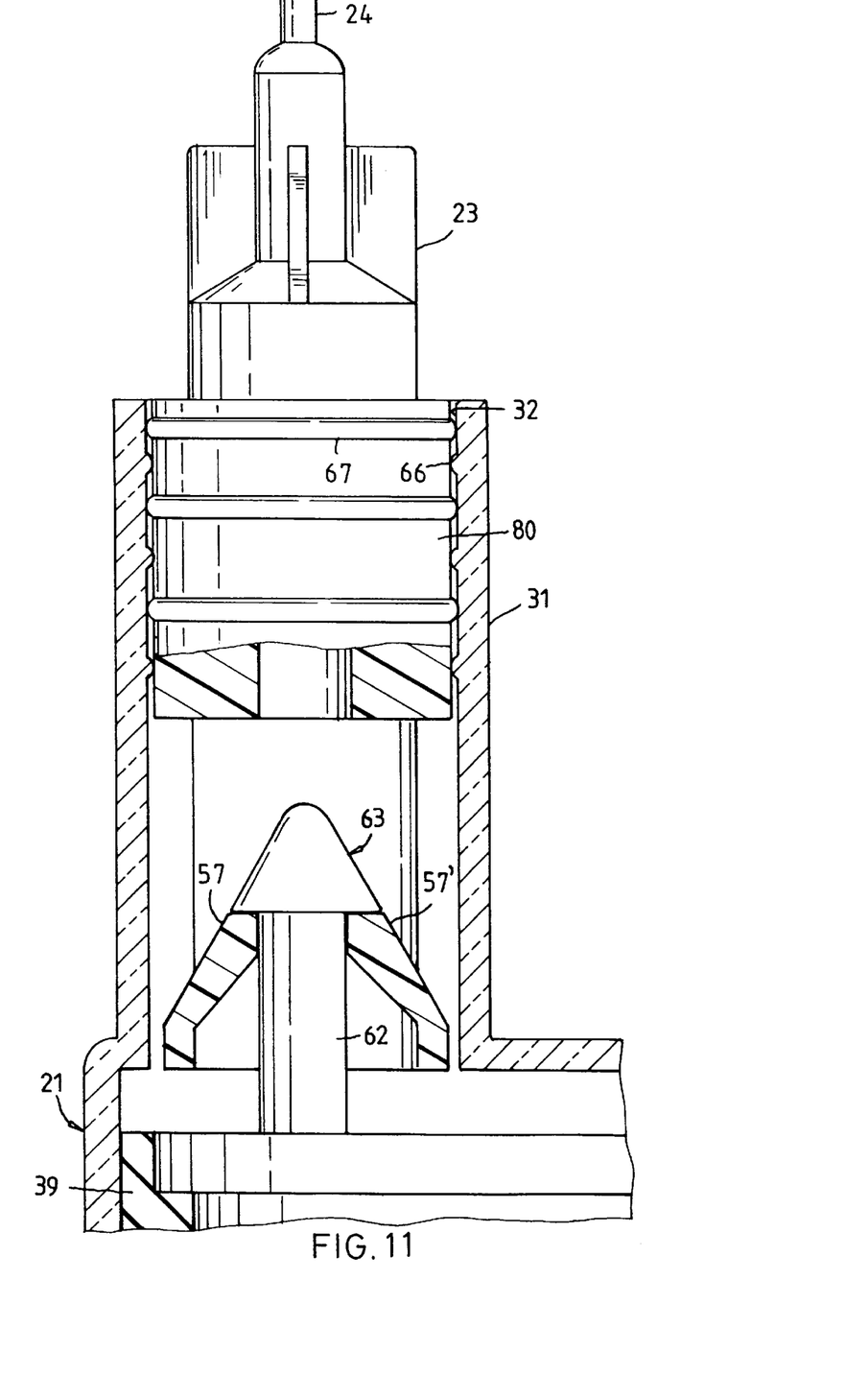
FIG. 11 is a partially enlarged sectional view of the second embodiment of the present invention.
Figure 12:
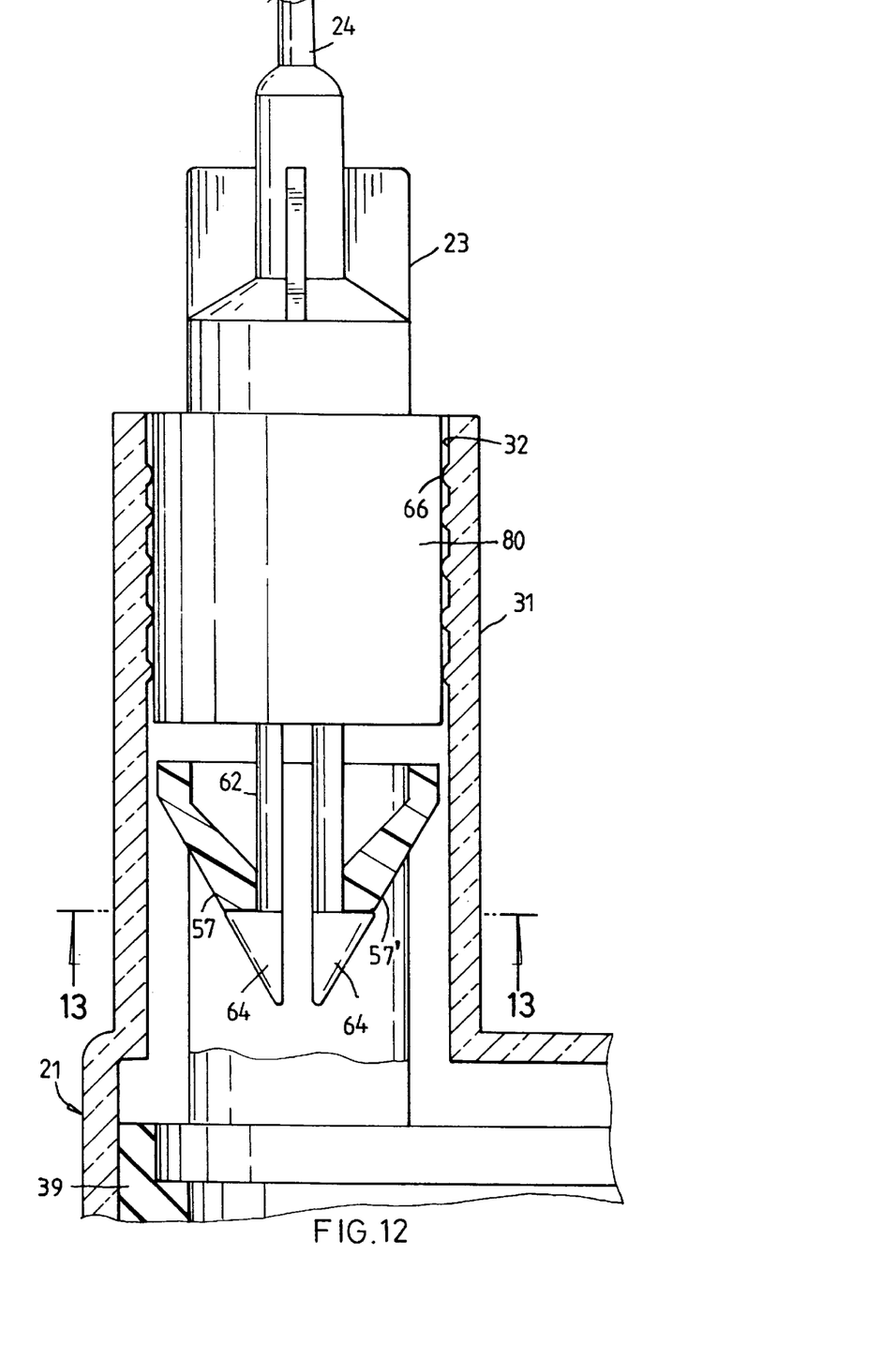
FIG. 12 is a partially enlarged sectional view of a third embodiment of the present invention.
Figure 13:
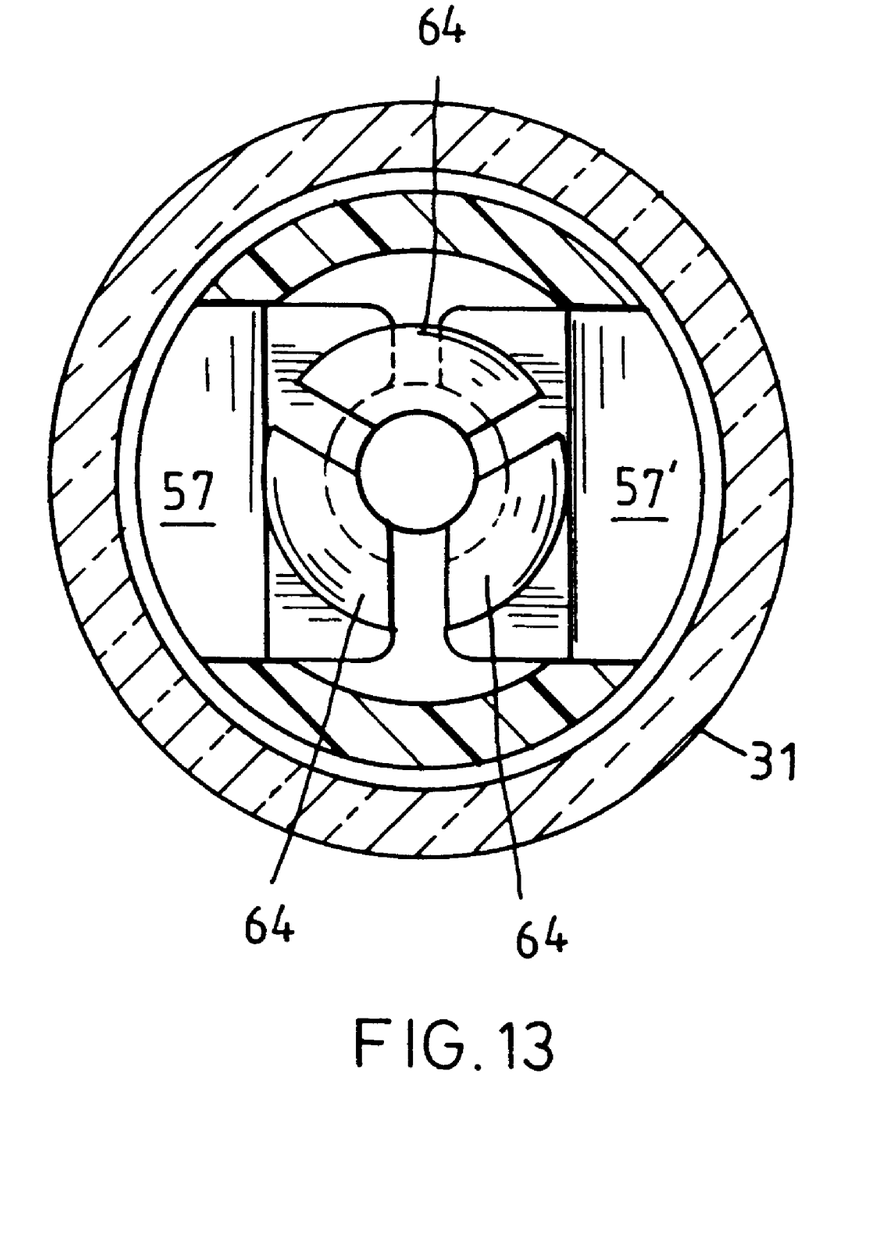
FIG. 13 is a sectional view taken along line 13—13 of FIG. 12.

The safety vein syringe 20 of the present invention can further include at least two radially arranged clicks 57, 57'. Please refer to FIGS. 10 to 12. If necessary, either of the inner wall of the needle holder cavity 32 and the outer wall of the fitting section 80 of the needle holder 23 can be disposed with one or more sealing rings 66, 67 sealedly engaged with the inner wall of the needle holder cavity 32 and the outer wall of the fitting section 80 of the needle holder 23.

Figure 5:
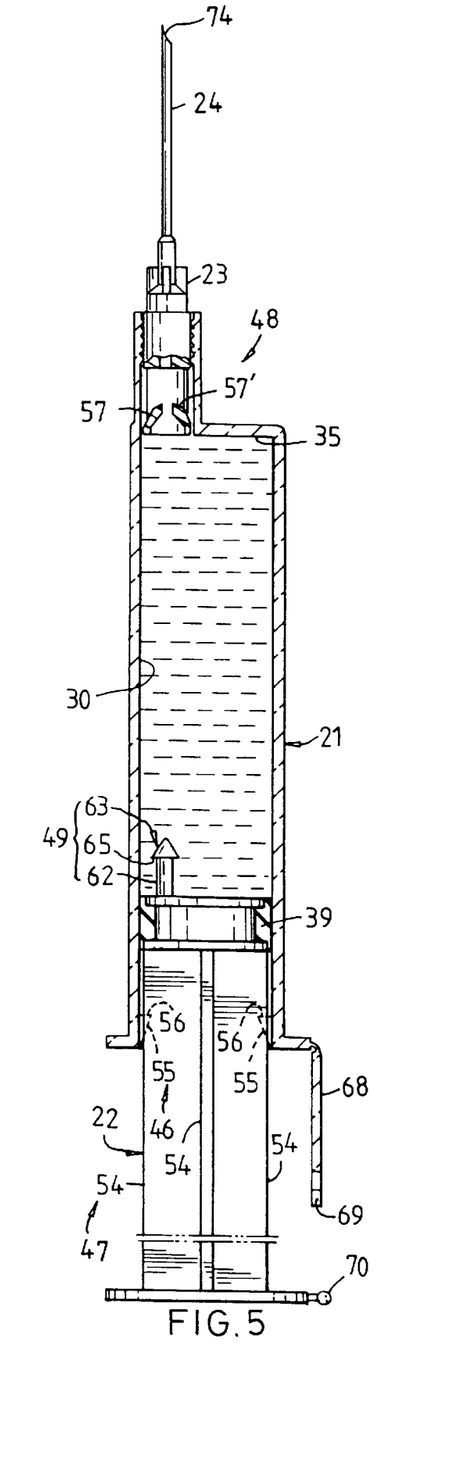
FIG. 5 is a longitudinally sectional view showing that the liquid medicine is sucked into the barrel of the first embodiment.
Figure 6:
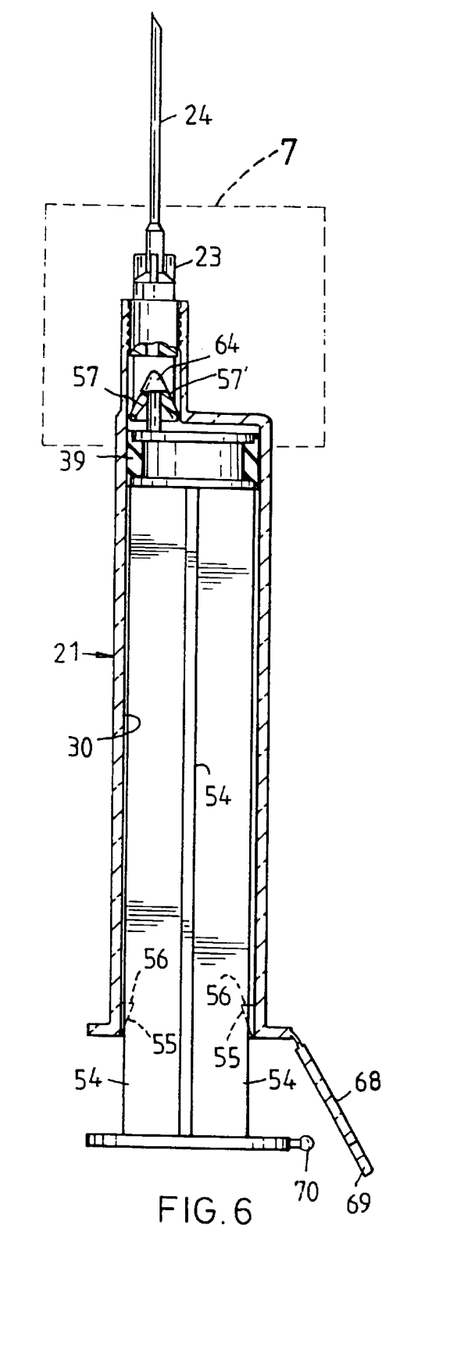
FIG. 6 is a longitudinally sectional view showing that the liquid medicine is completely injected and the detent of the plunger is hooked with the click of the needle holder of the first embodiment.

Please refer to FIGS. 1 to 6. The safety vein syringe 20 of the present invention further includes a latch plate 68, a first latch section 69 and a second latch section 70. The latch plate 68 has a first end 71 and a second end 72. The first end 71 is connected with the second end 28 of the barrel 21. The first latch section 69 is disposed at the second end 72 of the latch plate 68, while the second latch section 70 is disposed at the second end 38 of the plunger 22. The second latch section 70 can be latched with the first latch section 69 to locate the detent 63 near the click 57, 57' without latching with each other by mis-operation. In injection, the injection needle 24 is first thrusted into the liquid medicine and then the latch plate 68 is unlatched to pull the plunger 22 outward for sucking the liquid medicine into the barrel 21 (as shown in FIG. 5). Then the injection needle 24 is faced upward and the plunger 22 is slightly pushed upward for discharging the air in upper portion of the barrel 21 out of the tip 74 of the injection needle 24. Then the injection can be performed. After the injection is completed, as shown in FIGS. 6 and 7, the plunger 22 is pushed to the bottom and the detent 63 easily pushes open the clicks 57, 57' to hook therewith. The second distance 61 is less than the first distance 60 and the third distance 78 is less than the fourth distance 79 so that the clicks 57, 57' serve as ratchets. Accordingly, as shown in FIG. 7, when pulling back the plunger 22, the opposite clicks 57, 57' are depressed by the hook face 65 of the detent 63 to rotate about the bending sections 75, 75' in a direction shown by arrows 76, 76'. Therefore, the opposite clicks 57, 57' firmly clamp the stem of the detent 63. The greater the downward pulling force of the plunger 22 is, the greater the clamping force is. Therefore, the detent 63 is reliably firmly engaged with the clicks 57, 57' as shown in FIG. 7.

Figure 9:
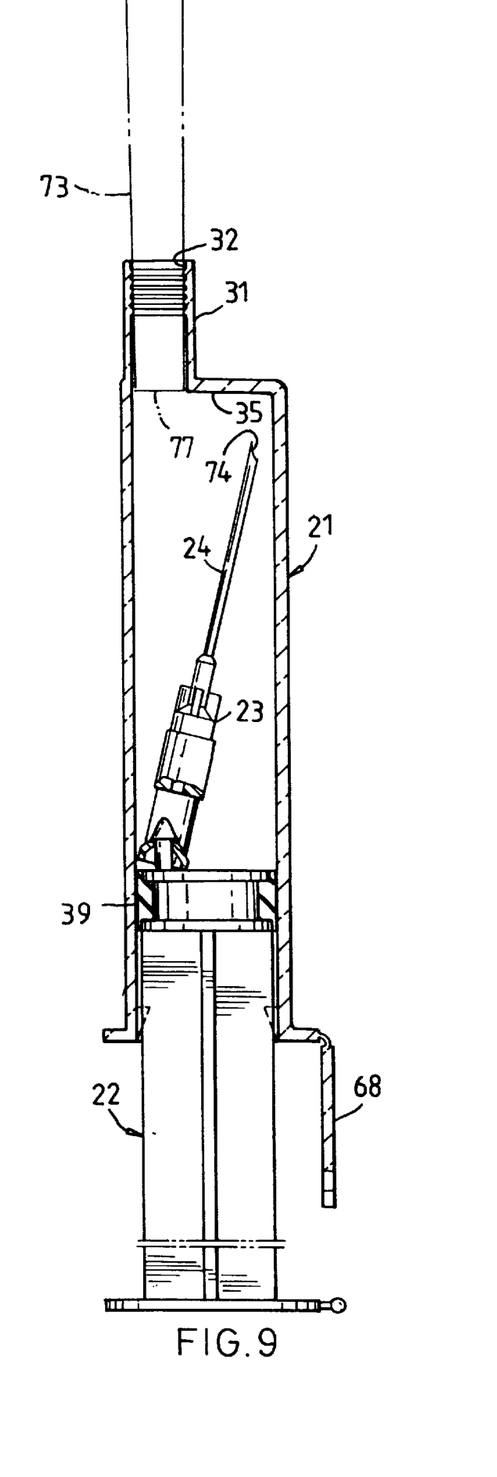
FIG. 9 is a longitudinally sectional view of the first embodiment, showing that after the liquid medicine is totally injected and the injection needles is pulled into the barrel, the injection needle tilts laterally.
Figure 10:
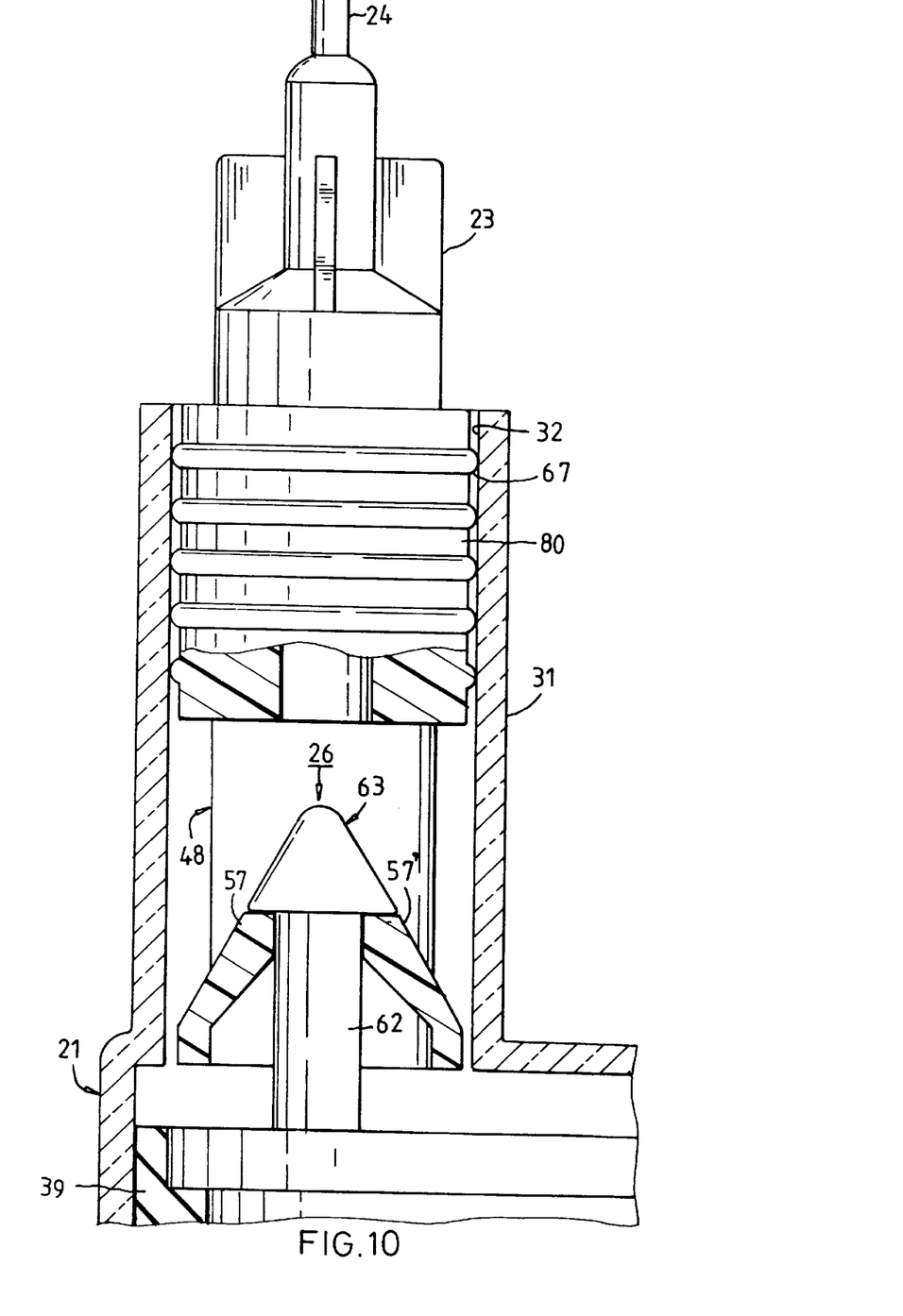
FIG. 10 is a partially enlarged sectional view of a second embodiment of the present invention.

As shown in FIG. 9, after the injection needle 24 is totally pulled back into the barrel 21, the detent 63 is loosely fitted with the clicks 57, 57'. Therefore, the tip 74 of the injection needle 24 will be unstably laterally tilted and positioned under the eccentrical shoulder section 35 of the barrel 21. Referring to FIG. 9, a tail end 77 of the needle sheath 73 with less diameter is inserted into the needle holder cavity 32 to seal the cavity 32 and prevent the tip 74 from extending out therefrom. At this time, the used syringe can be destroyed. Alternatively, with the tip 74 positioned under the shoulder section 35, the plunger 22 can be further pushed forward to press the tip 74 against the shoulder section 35 and bend the tip 74.

FIGS. 10 to 13 show a second embodiment of the present invention, which is identical to the first embodiment shown by FIGS. 2 to 9 except that the positions of the clicks 57, 57' and the detent 63 are exchanged.

According to the above arrangements, the present invention has the following advantages:

1. The guiding mechanism of the safety vein syringe is able to effectively solve the problem of deflection of the conventional injection needle. In addition, the leak-proof mechanism is able to avoid leakage of liquid medicine. Also, the safety vein syringe prevents the injection needle from unexpectedly detaching from the barrel. In addition, the injection needle can be easily pulled back into the barrel.
2. The safety vein syringe enables the plunger to easily firmly latch with the injection needle so as to reliably pull the injection needle into the barrel.
3. The safety vein syringe can avoid mis-latching of the injection needle prior to injection.

It is to be understood that the above description and drawings are only used for illustrating some embodiments of the present invention, not intended to limit the scope thereof. Any variation and derivation from the above description and drawings should be included in the scope of the present invention.

What is claimed is:

1. A safety vein syringe with retractable special needle, comprising:

(A) a syringe barrel having a first end, a second end and a first axis extending from the first end to the second end, the syringe barrel being formed with an internal barrel chamber surrounding the first axis by an equal distance, the first end of the barrel being disposed with a needle socket extending away from the first and second ends, the needle socket defining a needle holder cavity surrounding a second axis by an equal distance, the second axis being spaced from the first axis by a first distance, an eccentric annular shoulder section being formed between the barrel chamber and the needle holder cavity, the second end of the syringe barrel being formed with an opening;

(B) a plunger having a first and a second end, the first end being disposed with a piston and fitted into the barrel, the plunger having a centrally disposed third axis, after the plunger is installed into the barrel, the third axis coinciding with the first axis of the barrel, the first end of the plunger having a fourth axis spaced from the third axis by a second distance with is equal to the first distance;

(C) a needle holder having a first end and a second end, the second end of the needle holder being formed with a fitting section fitted in the needle holder cavity of the needle socket, the needle holder having a fifth axis coinciding with the second axis after the fitting section of the second end of the needle holder is fitted into the needle holder cavity;

(D) an injection needle inserted into the first end of the needle holder;

(E) a guiding mechanism including:
(a) a first guiding section disposed inside the second end of the barrel adjacent said opening, said first guiding section including at least a pair of projecting sections with at least a pair of guiding channels formed therebetween; and
(b) a second guiding section defined by at least a pair of outwardly directed ribs extending between the piston and the second end of the plunger, the ribs being respectively slidably fitted in the guiding channels to prevent rotation of the plunger relative to the barrel, whereby the plunger and the barrel can only be axially slid relative to each other with the fourth axis being maintained in coincidence with the second axis; and (F) a needle pulling mechanism including:
(a) a first needle pulling member having a first end and a second end, the first end of the first needle pulling member being integrally connected to the second end of the needle holder coincident with the fifth axis; and
(b) a second needle pulling member having a first end and a second end, the first end being connected to a portion of the first end of the plunger coincident with the fourth axis, the first and second needle pulling members being moved toward each other and hooked together when the plunger is slid within the barrel toward the first end thereof, whereby subsequent pulling of the plunger from the first end of the barrel toward the second end thereof pulls the needle holder together with the injection needle into the barrel.

2. The safety vein syringe as claimed in claim 1, wherein each of the projecting sections of the first guiding section further has a guiding slope face and a stopper face, the guiding slope face being inclined toward the opening of the second end of the barrel, the stopper face being substantially orthogonal to the first axis, whereby the piston can be slid into the barrel through the opening thereof along the guiding slope face, the stopper face serving to stop the piston from being removed from the barrel.

3. The safety vein syringe as claimed in claim 2, wherein the first guiding section includes four projecting sections with four guiding channels respectively formed therebetween, the four guiding channels being respectively spaced at 90 degree intervals.

4. The safety vein syringe as claimed in claim 3, wherein the second guiding section of the plunger is defined by two pairs of axially extending ribs forming a cross-shaped cross-sectional contour, the axially extending ribs being respectively slidably fitted in the four guiding channels of the first guiding section.

5. The safety vein syringe as claimed in claim 1, wherein the first needle pulling member includes a pair of clicks, each of the clicks having a first end and a second end, the first end being connected to the second end of the first needle pulling member, the second end of each click extending incliningly toward the fifth axis, a distance between the second ends of the pair of clicks defining a predetermined distance, the second needle pulling member having a stem extending from the second end thereof and a detent formed on the first end of the second needle pulling member, the detent being defined by a hook portion having a hook face extending radially outward to a proximal end of the hook portion, the proximal end having a diameter greater than the predetermined distance between the second ends of the pair of clicks and a diameter of the stem, the second needle pulling member engaging the first needle pulling member by the hook portion displacing the pair of clicks to separate the second ends thereof until the proximal end thereof passes the second ends of the pair of clicks and the pair of clicks return to engage the stem portion of the second needle pulling member, the proximal end of the hook portion being stopped against the second ends of the pair of clicks.

6. The safety vein syringe as claimed in claim 1, further comprising a latch plate, the latch plate having a first end connected to the second end of the barrel and a second end with a first latch section, a second latch section being disposed at the second end of the plunger and being latched with the first latch section to prevent the second needle pulling member from engaging the first needle pulling member by a mis-operation of the plunger, the second latching section being unlatched from the first latching section by a linear displacement of the second end of the plunger away from the second end of the barrel.

* * * * *